(12) United States Patent
Shober et al.

(10) Patent No.: US 6,214,365 B1
(45) Date of Patent: *Apr. 10, 2001

(54) METHOD OF PEST CONTROL AND ARTICLE USEFUL THEREFOR

(75) Inventors: Edward Wharton Shober; Sandra Metcalf Shober, both of Malmesbury (GB)

(73) Assignee: Demite Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,446

(22) Filed: May 24, 1999

Related U.S. Application Data

(63) Continuation-in-part of application No. 08/765,497, filed as application No. PCT/GB96/00672 on Mar. 20, 1996, now Pat. No. 5,916,580.

(30) Foreign Application Priority Data

Mar. 21, 1995 (GB) .................................................. 9505653

(51) Int. Cl.$^7$ ............................ A01N 25/00; A01N 25/34
(52) U.S. Cl. ........................... 424/405; 424/403; 8/115.7; 8/532; 8/922
(58) Field of Search ...................................... 424/405, 403; 8/115.7, 532, 922

(56) References Cited

U.S. PATENT DOCUMENTS 5,198,287 * 3/1993 Samson et al. .

FOREIGN PATENT DOCUMENTS

3220102 * 9/1991 (JP) .

OTHER PUBLICATIONS

*Pestic. Sci.* 1991, vol. 32, pp. 397–411, Steven W. Lindsay et al entitled Preliminary Studies on the Insecticidal Activity and Wash–Fastness of Twelve Pyrethroid Treatments Impregnated into Bednetting Assayed against Mosquitoes. Lindsay et al, 1991, Pestic. Sci., vol. 32, No. 4, pp. 397–411, 1991.*

* cited by examiner

*Primary Examiner*—Ali R. Salimi
(74) *Attorney, Agent, or Firm*—Breiner & Breiner

(57) ABSTRACT

House dust mites may be combatted by using a netting structure against a house dust mite habitat such as a mattress or cushion. The surfaces of the fibres of the yarns from which the netting structure is made carry particles of pyrethroid, preferably permethrin or deltamethrin.

6 Claims, 3 Drawing Sheets

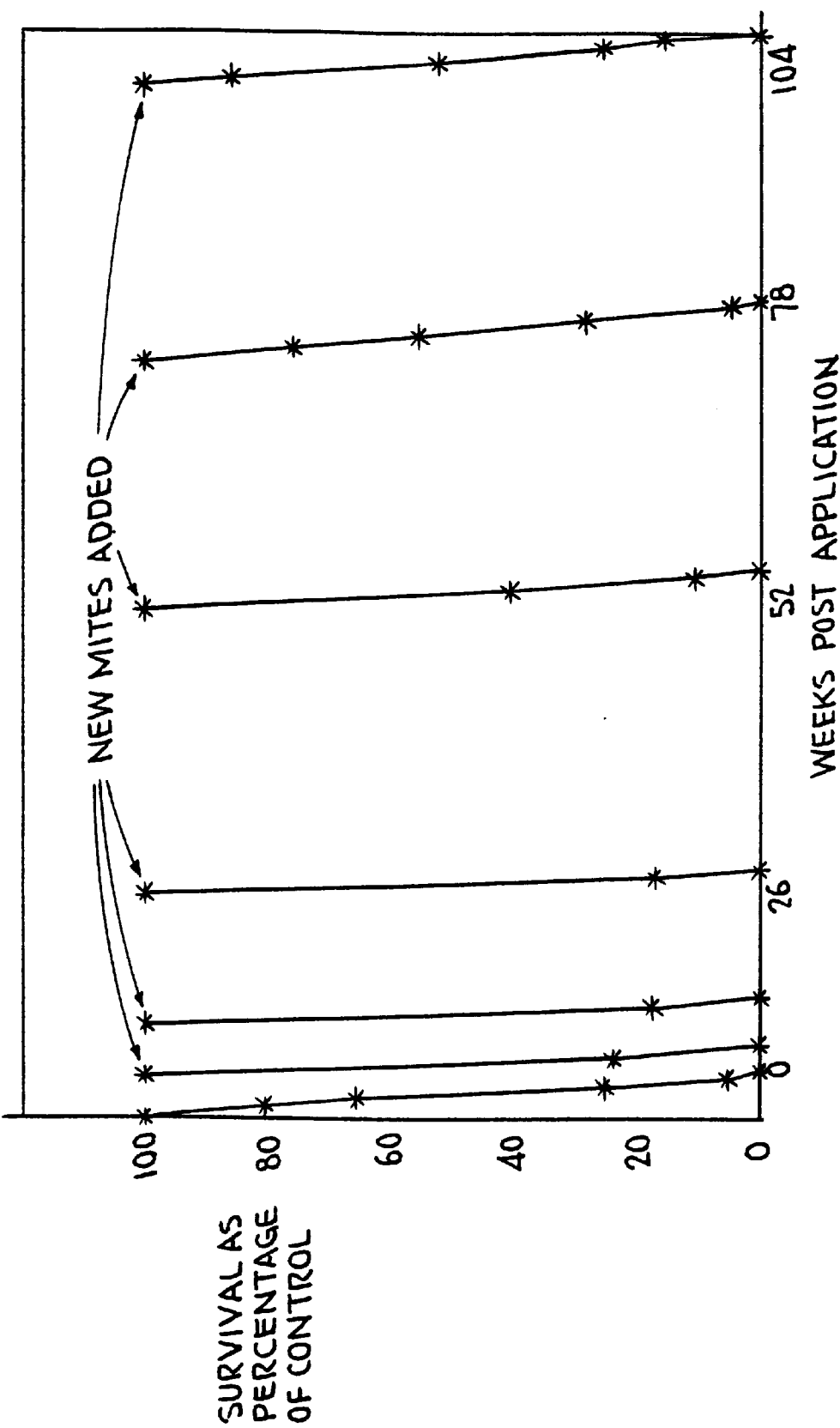

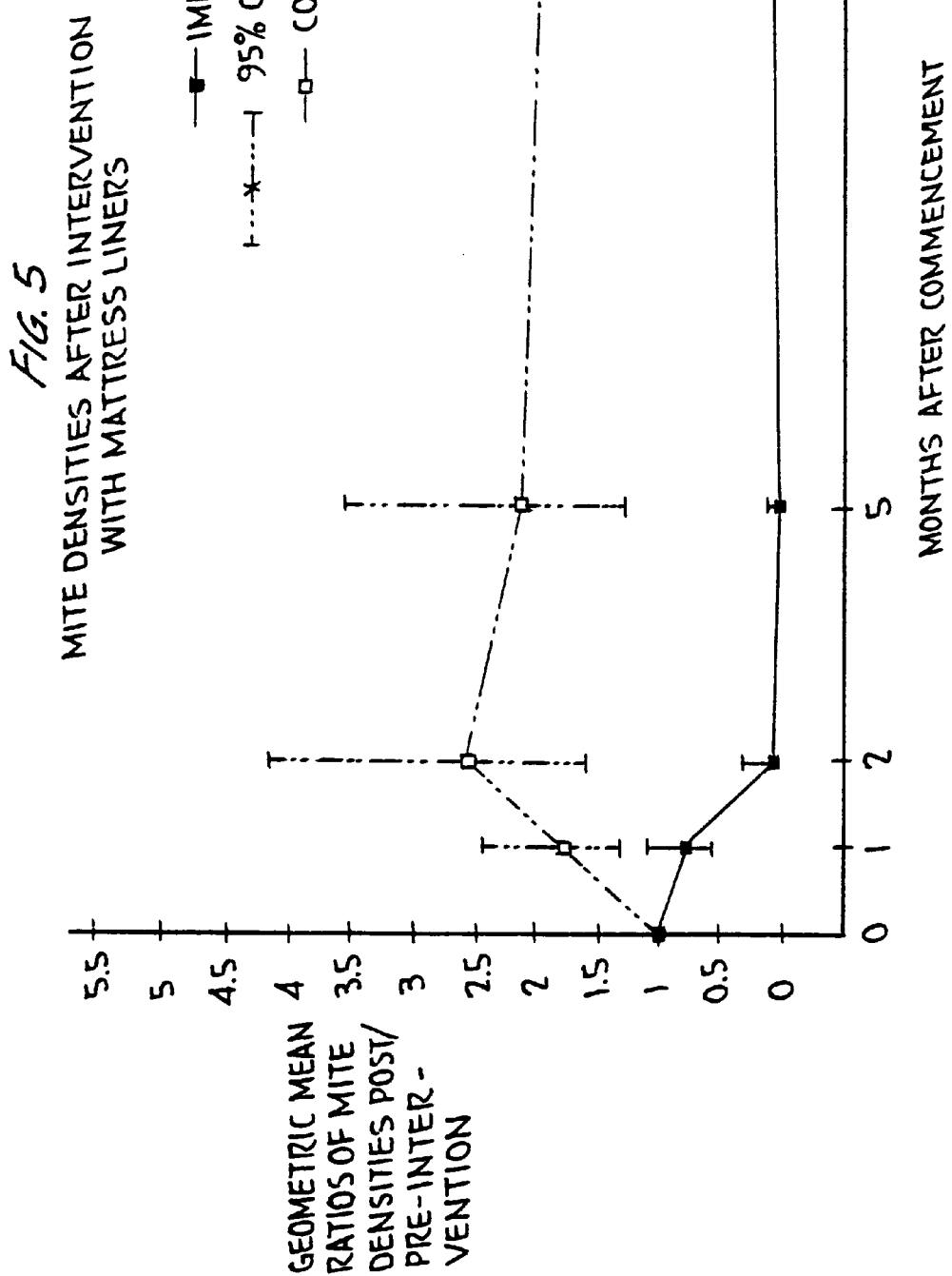

METHOD OF PEST CONTROL AND ARTICLE USEFUL THEREFOR

CROSS-REFERENCE TO RELATED APPLICATION

This application is a continuation-in-part of Application Ser. No. 08/765,497 filed on Jan. 9, 1997, (as PCT/GB96/00672) on Mar. 20, 1996, now U.S. Pat. No. 5,916,580.

FIELD OF THE INVENTION

The present invention related to the use of pesticide-impregnated linings and/or coverings to control house dust mite populations. In particular, the invention relates to pyrethroid-impregnated netting for use in covering, e.g. a mattress.

BACKGROUND TO THE INVENTION

The reported growth in house dust mite populations associated with domestic environments in Europe, the Americas, China and elsewhere is causing increasing concern. With the rising number of homes remaining at a constant favourable temperature and humidity, together with changes in house cleaning methods and types of bedding over the years, the numbers and survival of such creatures have risen sharply. House dust mites are scavengers on dead organic matter found in abundance in the home, feeding principally on the shed skin scales of humans. The mites, their faeces and products, are highly antigenic as contact or aero allergens in atopic diseases, e.g. eczema, asthma and allergic rhinitis. Mite allergy may trigger severe exacerbation that can be life-threatening in extrinsic asthma.

In addition, house dust mites have, in recent years, become an increased focus of concern as many experts consider them to be instrumental in initiating primary sensitisation leading to clinical asthma in very young children. It is believed that repeated exposure to the allergens produced by the mites can trigger early stages of asthma which will then become established as a chronic disease affected by a large range of different allergens in the environment.

There is also an overwhelming body of evidence that the presence of house dust mite faeces is instrumental in provoking asthma attacks in those with asthma or specific allergies, which cause immeasurable suffering, or even death.

House dust mites are to be found concentrated in many parts of the home, particularly soft furnishing, which provide them with a highly suitable environment. When they live in bedding, however, this brings them into the closest and most prolonged contact with humans. Pillows, duvets and mattresses have been found not only to house large populations of house dust mites, but also copious amounts of their faeces. The infestation cannot generally be removed by standard cleaning methods. The faecal pellets are particularly stable and resistant to removal from the fabric.

House dust mites are members of the family acaria, and one approach which could be contemplated to reduce the population of house dust mite would clearly be the use of an acaricide. However, in a domestic environment, this would cause many problems. For example, a well-known and highly effective acaricide is benzyl benzoate, but this is known to be very toxic to cats.

An alternative acaricide would be an organophosphate compound, some of which are well-know to be highly effective in eradicating mite infestation, particularly in farm animals. However, many such organophosphate compounds are toxic to humans and suspected, even at small exposures, to promote nervous system damage over the long term. Their use in domestic situations is accordingly not recommended.

In terms of the physical means used to reduce dust mite populations, one approach which has been suggested as acceptable in a domestic environment is that of using a dusting power containing suitable acaricide, and preparations have been made available commercially for this purpose, including some containing, as the acaricidal agent, pyrethroid compounds. These are know to be relatively non-toxic to humans, and have been much promoted, especially in domestic horticulture, as "natural insecticides". some (not all) display acaricidal properties as well as insecticidal ones. However, the use of dusting powder does not provide prolonged protection against infestation, and depends particularly on the efficiency of "dusting". In addition, the powder particles themselves may aggravate any asthmatic conditions which people coming into contact with them may have.

Control of insects in domestic environments has long been practised using impregnated textiles. Insecticide-impregnated netting has been used for decades as "mosquito netting", with a view of preventing the spread of malaria and other insect vector borne diseases, not only by denying the insect physical access to the human body, but additionally by killing insects on contact with the insecticide in the netting. Such an approach clearly does nothing to reduce infestation already present in beds and soft furnishings.

A suggestion has been made to incorporate into the fibres used to make synthetic fibre netting a mite-proofing component (Fumiyasu, Japanese Patent Publication 3-220102 published Sep. 27, 1991). However, this approach traps the component within the body of each fibre and although it will have an effect, it will be attenuated, not least because the active acaricidal component will only be released by slow vaporisation, and at very low (and thus ineffective) concentration.

GENERAL DESCRIPTION OF THE INVENTION

We have now found that effective control of house dust mite populations can be actioned by using an acaricide-impregnated netting, for example in the form of a net cover fitted around a mattress, pillow or like article of bedding or upholstery, and wherein the acaricide is present attached to the exterior surfaces of the fibres of the yarn making up the net.

Thus, in a first aspect, the present invention provides, for use in the control of house dust mites using a pyrethroid insecticide, a pre-formed netting structure wherein the netting structure is formed of yarns formed of a plurality of fibres, and wherein, attached to the exterior surfaces of the fibres, are particles of a pyrethroid acaricide. The netting structure is used by located it adjacent a surface, and preferably enclosing, a house dust mite habitat such as an article of bedding or upholstery.

When so constructed and used, any house dust mites emerging from the habitat can come into contact with the acaricide particles, with consequent lethal effect. In addition, as the netting is moved adjacent the habitat—e.g. by sitting on a cushion or getting into a bed—particles of the acaricide become detached from the fibres of the yarns forming the netting and permeate into the habitat, there to exert their lethal properties.

The netting structure of the invention may be made simply by impregnating preformed netting with a liquid formulation containing a pyrethroid acaricide, and drying the netting appropriately. It may then be applied around e.g. a pillow, mattress, duvet, cushion, bean bag or domestic pet bed, preferably by being first formed using conventional garment manufacturing techniques, into a close-fitting cover which covers at least a part, but preferably substantially the entire surface of the article.

A wide variety of pyrethroid compounds may be used in practising the present invention, including both natural and synthetic ones. The choice of which to use is conditioned, apart from the usual considerations of availability and price, by two main factors, effectiveness and toxicity. The effectiveness of pyrethroid compounds as acaricides varies; one with high effectiveness against mites should be chosen in preference to others. Since the compounds are to be used in situations where there will inevitably be human contact, ones with lower mammalian toxicity are preferably selected, provided they are adequately effective. Two particular pyrethroid compounds meet these criteria well, viz permethrin and deltamethrin, both of which are widely available.

The netting used may be made of any suitable fibre yarn, in particular nature fibres such as cotton or linen, or of synthetic yarns such as nylon or polyester. Mixed fibre yarns, including mixtures of natural and synthetic fibres may be used. The netting may be made by conventional textile manufacturing processes such as weaving or knitting.

the netting is impregnated, as indicated above, by using a liquid formulation containing the pyrethroid acaricide at a suitable concentration, and with the particles of the pyrethroid acaricide suitably dispersed therein, taking into account the particle size of the acaricide. The liquid composition may contain other agents such as a small quantity of binder to ensure weak adhesion of the particles to the fibres after drying, and anti-precipitation agents to stop the particles aggregating.

BRIEF DESCRIPTION OF FIGURES

The invention will now be described with reference to the following non-human examples, which refer to the figures in which:

FIG. 4 shows the effects of such netting covers on survival of house dust mites over an extended period, and the effect on newly introduced house mites at various time points; and FIG. 5 is a graph showing the density of mite infestation in mattresses covered with netting structures according to the invention.

SPECIFIC DESCRIPTION OF PREFERRED EMBODIMENTS

EXAMPLE 1

This example demonstrates by in vitro tests the efficacy of the netting structures according to the invention:

Two samples of 100% polyester netting were taken as follows:

Net A—196 Mesh, 100 denier.

Net B—196 Mesh, 75 denier.

Two different pyrethroid insecticides were also taken, both commercially available from Roussel Uclaf, Berkhampsted, Herts, UK. Sample 1 was a 10% by weight emulsifiable concentrate formulation of permethrin, and the other a 1% by weight sprayable composition containing deltamethrin. Both were water-based.

Squared of netting 25 cm×25 cm were impregnated by dipping into pyrethroid samples 1 and 2 diluted with water to a concentration which provided, when the samples had been dried for 48 hours at room temperature, a concentration of permethrin of 0.2 $g/m^2$ or of deltamethrin of 25 $mg/m^2$.

Figure 1:
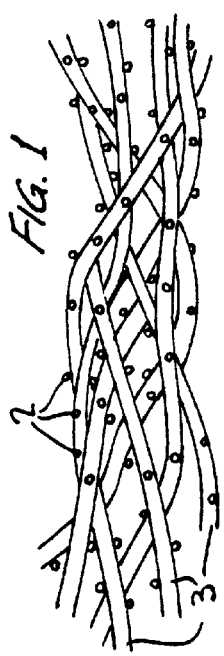
FIG. 1 is a diagrammatic view of a part of the fibre structure of a netting structure in accordance with the invention.

The dried net squares were then stored in foil at +4° C. until required for use. Microscopic examination of the samples showed a structure diagrammatically illustrated in FIG. 1, with particles of pyrethroid 2 on the surface of textile fibres 3.

Figure 2:
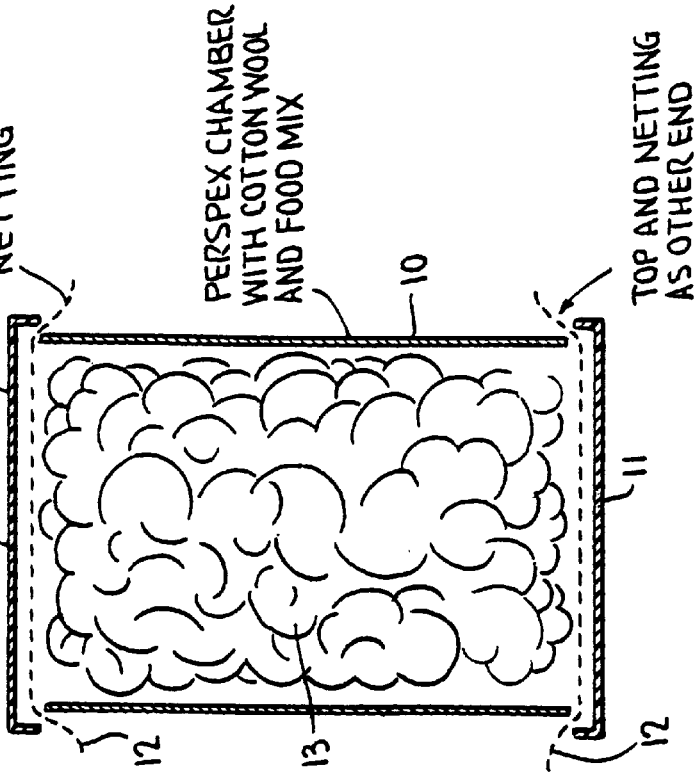
FIG. 2 shows an experimental mite holding chamber.

This example makes use of a mite holding chamber to stimulate conditions which would be expected from an impregnated net mattress cover in use. The mite-holding chamber used is illustrated in FIG. 2. It consists of a methyl methacrylate tube 10 with perforated lids on either end made of resilient plastics and holding the netting sample 12 across each end. The interior of the holding chamber formed by tube 10 was loosely packed with clinical grade non-absorbent cotton wool 13 and a plentiful supply of the mites' normal laboratory food, flaked fish food was included.

A nucleus of 500+ mites of mixed age and sex from the main breeding colony of the house dust mite Dermatophagoides farini held at the London School of Hygiene & Tropical Medicine were transferred into each week. When there were no living mites observed within the holding chamber, a further batch of mites was added and weekly observations continued.

As there are obviously inherent problems with identifying and counting such minute organism dispersed within a relatively large holding area, a standardised technique was used on each occasion as follows.

The plastic top of one end of the chamber was removed and the contents tipped into a clean petri dish. The cotton wool matrix was studied under a microscope for a period of 10 minutes during which time the proportion of live and dead mites was recorded. The matrix was then carefully replaced and the top secured before the next chamber was checked. Although this method does not give absolute mortality figures, it does provide a constant a relatively quick way of comparing the treatment types and ganging efficacy of the impregnated netting.

Figure 3:
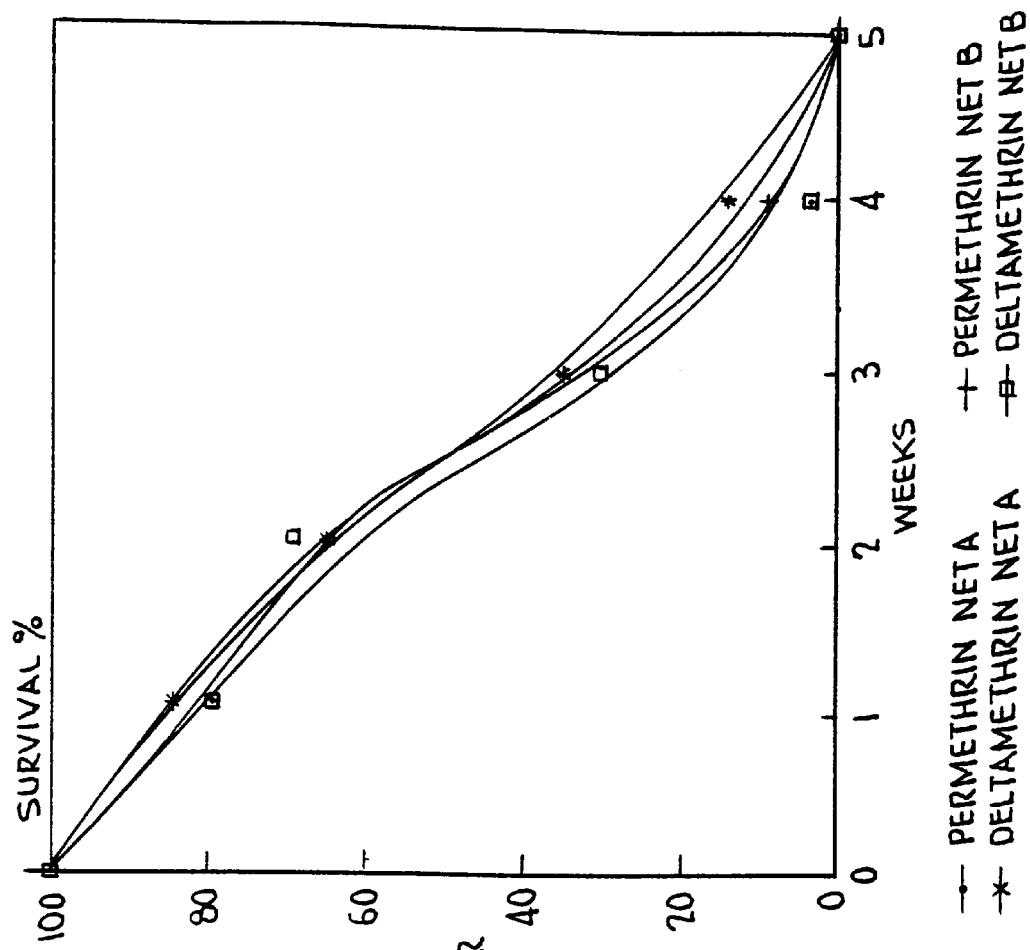
FIG. 3 is a graph showing the effects of pyrethroid-impregnated netting covers according to the present invention on the survival of house dust mites.

The results are shown in FIGS. 3 and 4 which show mortality and the effects of reinfestation against time.

FIG. 3 shows relative decline in living mite numbers with time for the four combinations of the two types of netting and the two pyrethroids. In every case there were not living mites in any treated netting chamber after 5 weeks.

FIG. 4 shows, for the permethrin impregnated net A, the mortality when a chamber was reinfested with an additional batch of mites following the total demise of the first of previous batch. As can be seen, in every case there was a very rapid decline in their numbers as revealed by subsequent inspections. This clearly shows the treatment's efficacy over a long time: even two years after the initial infestation, the efficacy of the netting to deal with reinfestation is clear.

It can be seen from FIG. 3 that both pyrethroids gave similar levels of mortality over time. The protection period is several months at least. FIG. 4 also clearly indicates that the effect takes several weeks to build up in the holding matrix, but once this is achieved, it acts relatively quickly on the subsequent mite infestation for at least a year.

These results therefore show that it is possible to reduce house dust mite numbers, or even eliminate enclosed populations using pyrethroid impregnated coverings over a prolonged period. The study shows complete mortality is achievable over long periods, at least of two years.

EXAMPLE 2

In this example, mattress covers were made by conventional fabrication techniques using standard "mosquito net" fabric following impregnation of that fabric with permethrin. The concentration of permethrin was 450 mg/m$^2$. "Control" mattress covers were made in the same fashion, but from unimpregnated fabric. These covers were then placed round mattresses which were regularly monitored to determine the house dust mite density therein.

FIG. 5 shows the results where along the vertical axis plotted the geometric mean ratio of measured mite density to that originally present at the start of the experiment, and the horizontal axis is calibrated in time in months. It can be seen that infestation dropped drastically in mattresses covered with the impregnated netting, while rising in those covered with unimpregnated netting.

What is claimed is:

1. A netting structure for reducing and/or eliminating a population of house dust mites using pyrethroid insecticide, comprising a preformed netting structure comprising yarns formed of a plurality of fibres, wherein attached to exterior surfaces of the fibres are particles of a pyrethroid acaricide in such a manner that said particles are physically released over time in use to come into contact with the population of house dust mites.

2. The netting structure of claim 1 constructed and arranged as a cover for entirely enclosing a pillow, mattress, duvet, cushion, bean bag or domestic pet bed.

3. The netting structure of claim 1 wherein the pyrethroid is permethrin and the particles thereof are deposited on the fibres by dipping netting in an aqueous emulsion containing permethrin, and causing or allowing the netting to dry.

4. The netting structure of claim 1 wherein the particles of pyrethroid are present in a concentration of 0.2 to 0.8 grams per square meter of the netting structure.

5. The netting structure of claim 1 wherein the fibres are of a polyethylene terephthalate.

6. A method of reducing and/or eliminating a population of house dust mites which includes locating a netting structure according to claim 1 against a surface of a house dust mite habitat and maintaining said structure against said habitat for a length of time to reduce and/or eliminate the population of house dust mites in said habitat.

* * * * *